(12) United States Patent
Mitsumori et al.

(10) Patent No.: US 6,494,222 B1
(45) Date of Patent: Dec. 17, 2002

(54) ULTRASONIC CLEANING APPARATUS FOR AN ENDOSCOPE

(75) Inventors: Naotake Mitsumori, Omiya (JP); Joji Watanabe, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 100 days.

(21) Appl. No.: 09/693,937

(22) Filed: Oct. 23, 2000

(30) Foreign Application Priority Data

Oct. 28, 1999 (JP) ........................................... 11-307286
Oct. 28, 1999 (JP) ........................................... 11-307287

(51) Int. Cl.⁷ ................................................. B08B 3/12
(52) U.S. Cl. ..................................................... 134/184
(58) Field of Search ............................... 134/1, 1.3, 184

(56) References Cited

U.S. PATENT DOCUMENTS 5,119,840 A  6/1992  Shibata 5,722,444 A  3/1998  Prokopenko et al.
5,865,199 A  2/1999  Pedziwiatr et al. .......... 134/184

FOREIGN PATENT DOCUMENTS

| DE | 24 55 964 A1 | 6/1975 |
| JP | 6-7290 | 1/1994 |
| JP | 126250 | 5/1994 |
| JP | A 11-56749 | 3/1999 |
| JP | 151198 | 6/1999 |

*Primary Examiner*—Philip Coe
(74) *Attorney, Agent, or Firm*—Oliff & Berridge, PLC (57) ABSTRACT

An ultrasonic cleaning apparatus of the present invention has a cleaning vessel which is made of a synthetic resin, while an ultrasonic vibration units are respectively disposed to face a hand control part, a top end, and a connector of an endoscope which is contained in the cleaning vessel. The ultrasonic vibration units individually have a diaphragm which is disposed at an opening of the cleaning vessel and ultrasonic vibrators which are adhered at the bottom of the diaphragm. An elastic body is provided between the cleaning vessel and the diaphragm.

10 Claims, 6 Drawing Sheets

ULTRASONIC CLEANING APPARATUS FOR AN ENDOSCOPE

BACKGROUND OF THE INVENTION

1. Field of the Invention

The present invention relates to an ultrasonic cleaning apparatus for an endoscope, more particularly to an ultrasonic cleaning apparatus for an endoscope of a type which cleans an endoscope immersed in a cleaning liquid with ultrasonic waves.

2. Description of Related Art

A typical endoscope requires cleaning and sterilization after the use. A cleaning apparatus for the endoscope cleans and sterilizes the entire endoscope by immersing the endoscope in a cleaning liquid or a sterilizing solution in a cleaning vessel. Japanese Patent Application Laid-open No. 6-7290 discloses an ultrasonic cleaning apparatus for an endoscope which cleans the endoscope by radiating ultrasonic waves from an ultrasonic vibrator. This ultrasonic cleaning apparatus uses a cleaning vessel that is made of stainless steel, because the cleaning vessel requires a strength as strong as being resistant to the radiation of the ultrasonic waves.

However, since the stainless cleaning vessel easily transmits vibrations of the ultrasonic waves, the ultrasonic waves radiated from the ultrasonic vibrators and the ultrasonic waves generated from the ultrasonic vibrators through the cleaning vessel interference with each other, and the cleaning efficiency is lowered.

Moreover, since the stainless cleaning vessel is heavy, the ultrasonic cleaning apparatus in its entirety must be heavy (e.g., about 105 kg), which causes the difficulty with moving the ultrasonic cleaning apparatus. Further, the cleaning vessel is arranged at a height of an operator's lower back, which is an upper part in the ultrasonic cleaning apparatus, thus the heavier the cleaning vessel is, the less stabilized the device is, because the device has a center of gravity at the upper part of itself. Furthermore, the ultrasonic cleaning apparatus must be large in its entirety because the heavier the cleaning vessel is, the sturdier the frame needs to be for supporting the cleaning vessel.

In addition, the conventional ultrasonic cleaning apparatus for an endoscope cleans the endoscope by radiating an ultrasonic wave of one type of frequency. However, contamination in the endoscope differs depending on sections such as a top end, a hand control part, and a connector part, and besides, the sections of endoscope differ in shape. Because of that, despite radiating an ultrasonic wave of one type of frequency, the entire endoscope cannot be efficiently cleaned.

As a cleaning apparatus using an ultrasonic wave, an ultrasonic cleaning apparatus is known which changes ultrasonic waves of plural frequencies one at a time for a certain time period so as to clean the endoscope. Yet, because the ultrasonic cleaning apparatus radiates ultrasonic waves of plural frequencies one by one, the device takes a long time for cleaning.

SUMMARY OF THE INVENTION

The present invention has been developed in view of the above-described circumstances, and has as its object the provision of an ultrasonic cleaning apparatus for an endoscope which can prevent the cleaning efficiency from being lowered due to the interference of the ultrasonic waves while providing a light-weighted cleaning vessel. The present invention also aims at providing an ultrasonic cleaning apparatus for an endoscope that can efficiently clean the entire endoscope in a short period of time.

In order to achieve the above-described objects, the present invention is directed to an ultrasonic cleaning apparatus for an endoscope, comprising: a cleaning vessel made of synthetic resin, the cleaning vessel holding a cleaning liquid in which the endoscope is immersed; and an ultrasonic generator which applies ultrasonic waves to the cleaning liquid so as to clean the endoscope, the ultrasonic generator comprising an ultrasonic vibrator and a diaphragm, the ultrasonic vibrator being attached to the cleaning vessel through the diaphragm.

According to the present invention, a resin cleaning vessel which transmits less vibration than metal is used; thus the vibration caused by the ultrasonic wave is not easily transmitted through the cleaning vessel, and the cleaning efficiency is not lowered due to the interference of the ultrasonic waves. As a result, the endoscope can be efficiently cleaned.

The cleaning Vessel is made of synthetic resin, so that the cleaning vessel can be light-weighted. Thus, the present invention can achieve the light-weighted and small-sized ultrasonic cleaning apparatus as well as stabilizing the device by positioning the center of gravity of the device at a bottom part of the device.

The ultrasonic vibrator is attached to the resin cleaning vessel through the diaphragm; thus the resin cleaning vessel is not damaged by the vibration caused by the ultrasonic wave, unlike the case where the ultrasonic vibrator is directly attached to the resin cleaning vessel.

Preferably, a plurality of ultrasonic vibrators are arranged to face sections where the contamination is high in the endoscope which is contained in the cleaning vessel, thus the cleaning apparatus can concentrate cleaning to the sections where the contamination is high.

The ultrasonic cleaning apparatus securely prevents the cleaning vessel from being damaged by placing an elastic body between the cleaning vessel and the diaphragm, because the vibrations that the cleaning vessel receives are reduced by the diaphragm.

Preferably, by making the diaphragm with metal (e.g., stainless steel or titanium), the ultrasonic vibrators do not fall off which causes lowered cleaning efficiency, because the metal ultrasonic vibrators can be securely adhered to the diaphragm.

Preferably, the ultrasonic cleaning apparatus further comprises at least one additional ultrasonic generator applying ultrasonic waves of a different frequency from the former ultrasonic generator. Thus, the entire endoscope can be efficiently cleaned by simultaneously radiating ultrasonic waves of optimum frequencies for the respective sections of the endoscope.

The plural ultrasonic vibrators with different frequencies may be attached to one diaphragm; thus, a computed intermingled wave can be formed without noises of other diaphragms. In the present invention, plural cleaning effects can be achieved at the same time like a case where the ultrasonic waves with different frequencies are radiated one at a time for a certain time period. The device of the present invention can thereby efficiently clean the endoscope in a short period of time.

The ultrasonic cleaning apparatus of the present invention also inhibits the vibration caused, by the ultrasonic waves to be transmitted from the respective ultrasonic vibration units through the cleaning vessel by making the cleaning vessel with synthetic resin. Therefore, the ultrasonic waves radiated from the ultrasonic vibration units are inhibited to interference with each other.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENT

Hereunder the preferred embodiments of the ultrasonic cleaning apparatus for an endoscope of the present invention will be described in accordance with the accompanied drawings.

Figure 1:
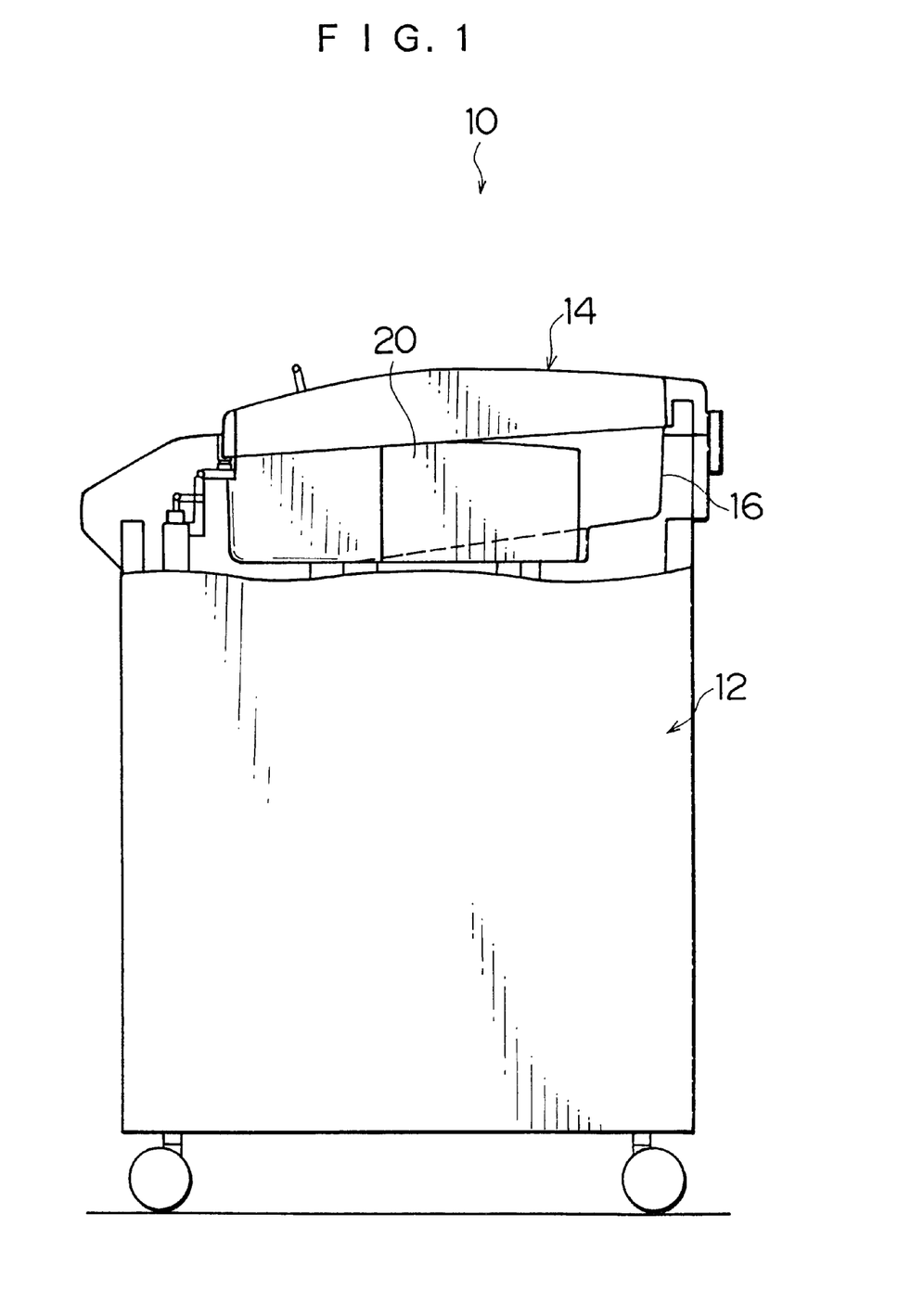
FIG. 1 is a side view showing the first embodiment of an ultrasonic cleaning apparatus for an endoscope of the present invention.
Figure 2:
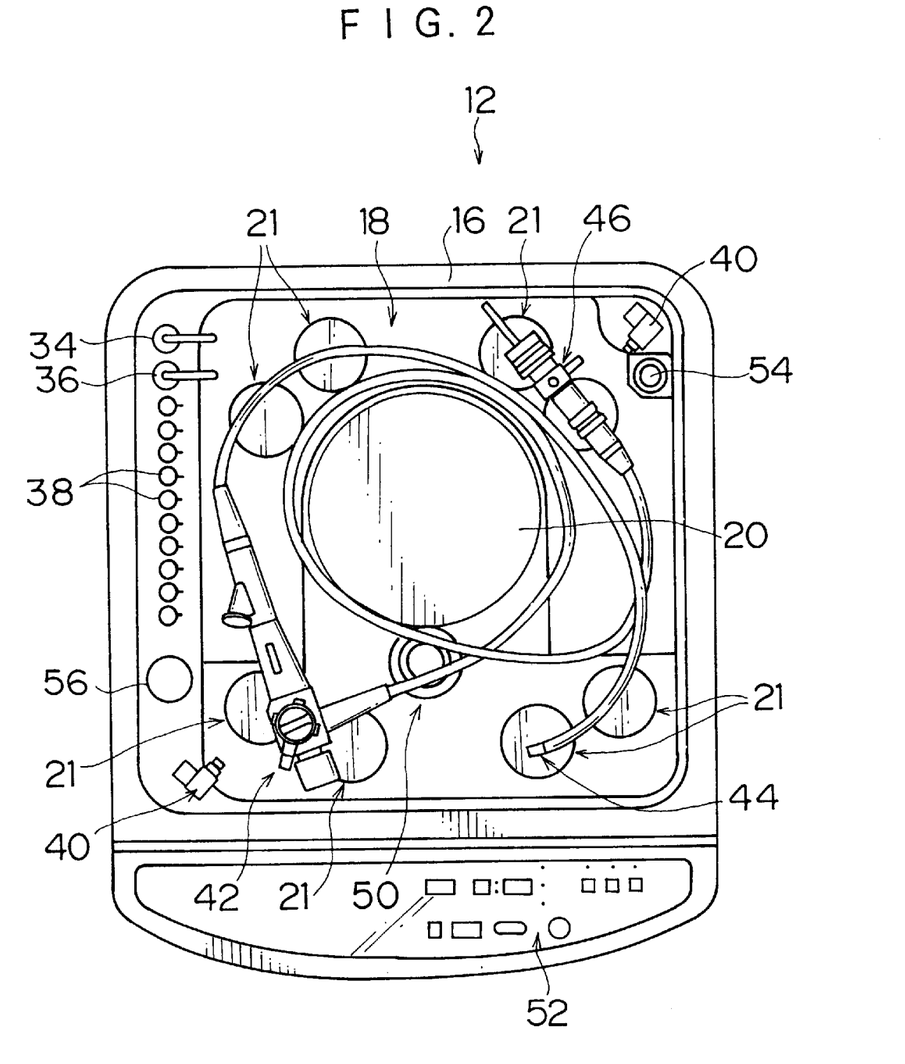
FIG. 2 is a plan view of the entire ultrasonic cleaning apparatus in FIG. 1.

As shown in FIGS. 1 and 2, an ultrasonic cleaning apparatus 10 of the first embodiment with a box-shaped outer appearance comprises a body 12 and a lid 14. A cleaning vessel 16 is provided at the top of the body 12, and an endoscope 18 which requires cleaning is contained in the cleaning vessel 16.

The lid 14, which can be opened and closed, is attached to the upper part of the device 12 by a hinge or the like. The upper opening of the cleaning vessel 16 is completely covered by closing the lid 14, so that a cleaning liquid (e.g., water or detergent) and an antiseptic solution supplied to the cleaning vessel 16 are not splashed to outside.

The cleaning vessel 16 is molded by synthetic resin that is resistant to the antiseptic solution (e.g., composed by glutaraldehyde, peracetic acid, acidic water, chlorine dioxide, hydrogen peroxide, and so forth) such as FRP (Fiberglass Reinforced Plastics), polyacetal, polyphenyleneoxide, acrylonitrile-butadiene-styrene copolymer, polyethylene, polypropylene, and PTFE (PolyTetraFluoroEthylene), polycarbonate.

A cylindrical jetting apparatus 20 is provided at the center of the cleaning vessel 16, and a nozzle (not shown) is disposed at the side of the jetting apparatus 20. As activating the jetting apparatus 20, the jetting apparatus 20 rotates while the cleaning liquid is jetted from the nozzle, and the endoscope 18 that is contained in the cleaning vessel 16 is cleaned by the swirling current.

A plurality of ultrasonic vibration units 21 are disposed at the bottom of the cleaning vessel 16. The ultrasonic vibration units 21 are disposed at the proximity of the sections where contamination of the endoscope 18 which is contained in the cleaning vessel 16 is high. More specifically, a pair of the ultrasonic vibration units 21 are disposed at the position where a hand control part 42 of the endoscope 18 is positioned, another pair of the ultrasonic vibration units 21 are disposed at the position where a top end 44 of an insertion part is positioned, and still another pair of the ultrasonic vibration units 21 are disposed at the position where a connector 46 is positioned. The pair of the ultrasonic vibration units 21 at the upper left corner of the cleaning vessel 16 is used for cleaning two endoscopes 18 simultaneously.

Figure 3:
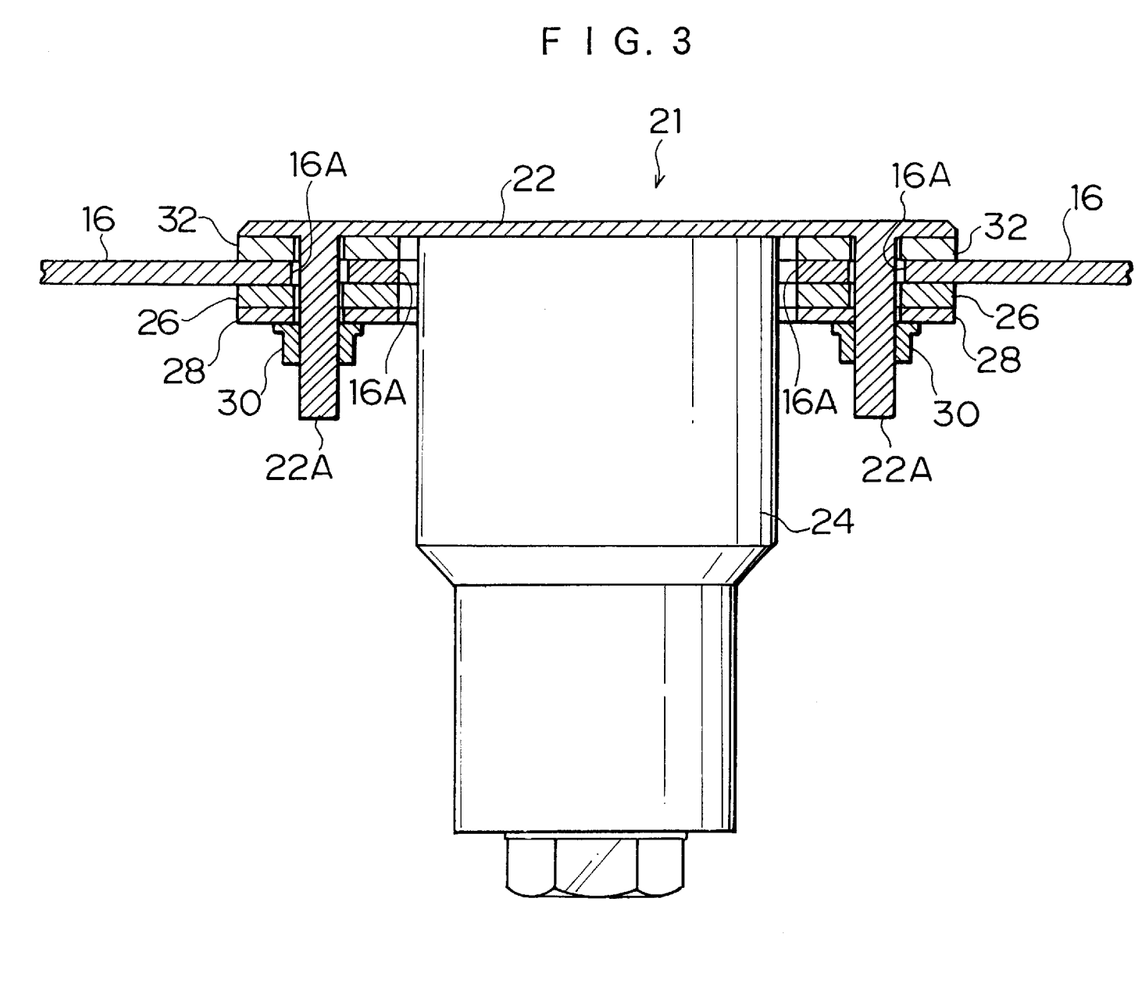
FIG. 3 is a longitudinal section view of the ultrasonic cleaning apparatus in FIG. 2.

As shown in FIG. 3, the ultrasonic vibration unit 21 is provided with a diaphragm 22 and an ultrasonic vibrator 24. The diaphragm 22 is placed so as to block a circular opening 16A, which is formed at the bottom of the cleaning vessel 16. The diaphragm 22 is made of metal such as stainless steel or titanium, and is fixed to the cleaning vessel 16 by tightening nuts 30 via packings 26 and pressing plates 28.

The ultrasonic vibrator 24 is of a Langevin-type, and is attached by adhering to the bottom of the diaphragm 22. As the ultrasonic vibrator 24 vibrates, the ultrasonic wave is radiated in the cleaning vessel 16 through the diaphragm 22.

An elastic body 32 is disposed between the diaphragm 22 and the cleaning vessel 16, so that a gap between the diaphragm 22 and the cleaning vessel 16 is sealed by the elastic body 32. The elastic body 32 is made of a material that is resistant to the cleaning solution such as fluoric rubber, silicone rubber, EPDM (Ethylene-Propylene-Diene-Methylene=EPT: Ethylene-Propylene Terpolymer), silicone filler, and elastic fluoric resin. Except the elastic body in between the diaphragm 22 and the cleaning vessel 16, any elastic body at a position to be immersed into the cleaning solution is made of the above-mentioned rubber material. On the other hand, an elastic body which is not at a position to be immersed into the cleaning solution (e.g. the packing 26) may be made of rubber material that is not mentioned above, such as neoprene rubber.

As shown in FIG. 2, a cleaning solution injecting opening 34, a detergent injecting opening 36, and a plurality of couplers 38 are provided at the side of the cleaning vessel 16. The cleaning solution is injected from the cleaning solution injecting opening 34 at a time of cleaning with the cleaning solution, and the detergent is injected from the detergent injecting opening 36 at a time of current cleaning. The coupler 38 is also connected with a mounting opening for an air/water supply button and an insertion opening for a forceps which are provided at a hand control part 42 of the endoscope 18 via a tube (not shown). The air/water supply tube, a suction tube, forceps insertion tube, and so forth, in the endoscope 18 can be cleaned by the cleaning water and disinfectant solution which are supplied from the couplers 38.

At the corners which face at each other of the cleaning vessel 16, a pair of shower nozzles 40 and 40 are provided, and water and other liquids are jetted from the shower nozzles 40 and 40. At the bottom of the cleaning vessel 16, a discharge opening 50 is provided, and the cleaning liquid and solutions which are supplied in the cleaning vessel 16 are discharged by opening the discharge opening 50 with an electromagnetic valve (not shown).

As seen again from FIG. 2, at the front of the body 12, an operation/display panel 52 is arranged, which is provided with number of buttons for instructing respective settings related to the contents of the cleaning operations and the start of cleaning. The operation/display panel 52 also displays respective contents such as a remaining time for cleaning, a time until the completion of an operation, and warning at the time of trouble.

A reference number 54 in FIG. 2 is a liquid level sensor, which detects a liquid level so as to prevent the detergent and cleaning solution from flooding out of the cleaning vessel 16. A reference number 56 is a discharge opening for the overflow.

Next, an operation will be described of the ultrasonic cleaning apparatus for an endoscope which is constructed as described above.

As presented in FIG. 2, an operator first puts the endoscope 18 in the cleaning vessel 16 so that the endoscope 18 is wound around the jetting apparatus 20. The operator secondly connects the mounting opening for the air/water supply button of the endoscope 18 and the forceps inserting opening to the couplers 38 via tubes (not shown). After closing the lid 14, the operator starts the cleaning process by operating the operation/display panel 52.

Figure 4:
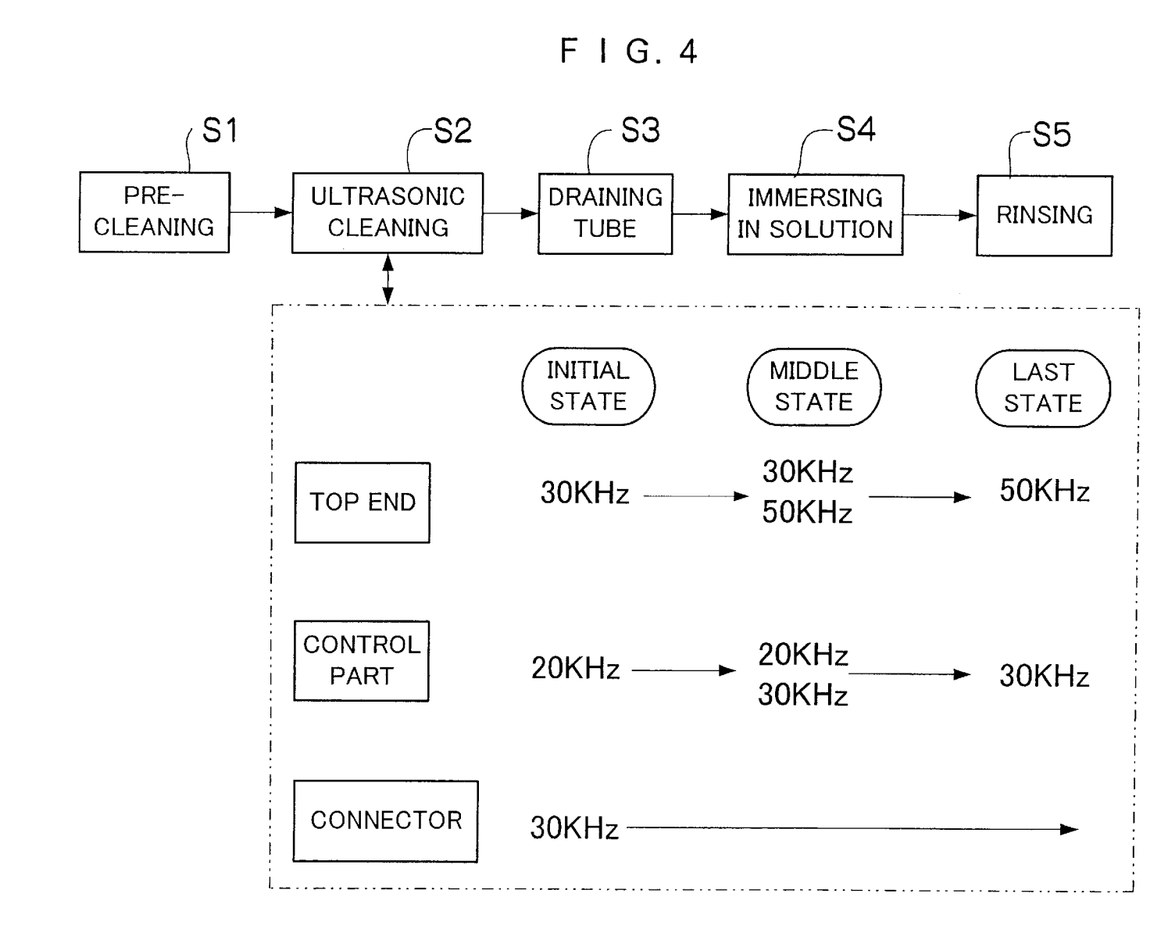
FIG. 4 is a flowchart showing a cleaning process of the ultrasonic cleaning apparatus for an endoscope of the present invention.

As shown in FIG. 4, a pre-cleaning of the endoscope 18 is performed in the cleaning process (Step 1). In the pre-cleaning process, for example, water is jetted from the nozzles by activating the jetting apparatus 20 so as to perform current cleaning on the external surface of the endoscope 18, and internal routes of the tubes of the endoscope 18 are cleaned by injecting water in the routes. The external surface of the endoscope 18 may also be cleaned at this point by jetting water from the shower nozzles 40 and 40, and also the pre-cleaning may be performed with deter gent by injecting the detergent from the detergent injecting opening 36. The water used for the pre-cleaning is discharged from the discharge opening 50 afterwards.

After the pre-cleaning, the ultrasonic cleaning for the endoscope is performed (Step 2). In the ultrasonic cleaning, the cleaning solution (water or detergent) is held in the cleaning vessel 16, and the endoscope 18 is completely immersed into the cleaning solution. The ultrasonic vibrators 24 vibrate and the ultrasonic waves are applied from the diaphragm 22 to the cleaning solution in the cleaning vessel 16. The endoscope 18 is thereby cleaned by the cavitation generated by the ultrasonic waves. Since each of the hand control part 42, the top end 44, and the connector 46 of the endoscope 18 where the contamination is relatively high is arranged at the upper part of each ultrasonic unit 21, the endoscope 18 can be efficiently cleaned at this point by the ultrasonic wave radiated from the ultrasonic vibrators 24. The frequency of the ultrasonic wave radiated from each of, the ultrasonic vibrators 24 is designated depending on the section of the endoscope 18 that is arranged at the upper part of each of the ultrasonic vibrators 24. The designation of the frequency will later be described in detail.

After the ultrasonic cleaning process, the cleaning solution in the cleaning vessel 16 is, discharged through the discharging opening 50, and the inside of the tubes of the endoscope 18 are drained (Step 3). Next, the water is supplied in the cleaning vessel 16 so as to supply the water through the external surface and the inside of the tubes of the endoscope 18, and the contamination in the endoscope 18 and, the cleaning vessel 16 are washed out. Then, the drying is performed in order to prevent the disinfectant from being diluted, and now the process for immersing in the disinfectant is performed (Step 4).

In the process for immersing in the disinfectant, the disinfectant is injected from the solution injecting opening 34 to the cleaning vessel 16 while injecting the disinfectant from the coupler 38 to the internal routes of the tubes of the endoscope 18, whereby the entire endoscope 18 is sterilized. After the sterilization, rinsing is performed (Step 5), and at last the air or alcohol is supplied to the cleaning vessel 16 so as to dry the endoscope 18. The cleaning process of the endoscope 18 is completed by the above-described steps.

Now, the designating the frequencies of the ultrasonic waves which are radiated from the ultrasonic vibrators 24 will be described.

Ultrasonic waves differ in cleaning efficiency depending on frequencies. For example, an ultrasonic wave with low frequency has a large cavitation, thus is suitable for cleaning a large section and clearing persistent contamination. An ultrasonic wave with a high frequency, in contrast, has a small cavitation, thus is suitable for cleaning a small section and clearing minute contamination.

Because the endoscope 18 has different sizes and degrees of contamination depending on sections, an optimum frequency for cleaning naturally differs. For example, the top end 44 is a small section in which minute contamination must be cleared; thus, an ultrasonic wave with a high frequency (e.g. 30–50 kHz) is suitable. Thus, an ultrasonic wave of 30 kHz is radiated first by the two ultrasonic vibrators 24 and 24 that face the top end 44, and the contamination at the top end 44 is roughly cleaned. Next, one of the ultrasonic vibrators 24 radiates an ultrasonic wave of 30 kHz while the other ultrasonic vibrator 24 radiates an ultrasonic wave of 50 kHz, and the top end 44 is cleaned by an intermingled ultrasonic wave of 30 kHz and 50 kHz. Thereby, not only persistent contamination is cleared by the ultrasonic wave of 30 kHz, but also minute contamination can be cleared by the ultrasonic wave of 50 kHz. At last, the ultrasonic wave of 50 kHz is radiated from both ultrasonic vibrators 24 and 24 so as to clear the minute contamination at the top end 44.

As presented above, the top end 44 is cleaned by ultrasonic waves of relatively high frequency while minute contamination is cleared gradually by increasing the frequencies of the ultrasonic waves step by step; thus the top end 44 can be efficiently cleaned. Moreover, the two ultrasonic vibrators 24 and 24 simultaneously radiate ultrasonic waves of different frequencies for cleaning, so that unevenness of cleaning can be eliminated compared with cleaning with an ultrasonic wave of a single frequency.

As to the hand control part 42 of the endoscope 18, since it is a large section and requires clearing persisting contamination, the cleaning with the ultrasonic wave of a low frequency (e.g. 20–30 kHz) is suitable. Thus, first, an ultrasonic wave of a low frequency of 20 kHz is radiated by the two ultrasonic vibrators 24 and 24 that face the hand control part 52, and second, one of the ultrasonic vibrators 24 radiates an ultrasonic wave of 20 kHz while the other ultrasonic vibrator 24 radiates an ultrasonic wave of 30 kHz, then both ultrasonic vibrators 24 and 24 radiate an ultrasonic wave of 30 kHz. Thereby, the hand control part 42 can be efficiently cleaned like the top end 44 without generating the unevenness.

Since the connector 46 is a large section, an ultrasonic wave of low frequency (e.g. 20–30 kHz) is suitable for cleaning the section. The ultrasonic wave of thus 30 kHz is radiated by the ultrasonic vibrators 24 and 24 that face the connector 46. The connector 46 is not very contaminated compared with the top end 44 and the hand control part 42; thus the connector 46 can be cleaned without lowering the frequency of the ultrasonic wave or forming the intermingled wave.

Since the cleaning vessel 16 is made of a resin that does not easily transmit vibrations, even though the plural ultrasonic vibration units 21, 21, . . . radiate ultrasonic waves of different frequencies, the ultrasonic waves are not transmitted through the cleaning vessel 16 and the ultrasonic waves do not interference each other. Therefore, the cleaning efficiency is not lowered by the interference of the ultrasonic waves, and the endoscope 18 can be efficiently cleaned.

As presented above, the ultrasonic cleaning apparatus 10 of the present invention uses the cleaning vessel 16 made of resin, which does not easily transmit the vibrations. Thus, even though the ultrasonic waves of different frequencies are radiated to the hand control part 42, the top end 44, and the connector 46 of the endoscope 18, the ultrasonic waves do not interfere with each other and the respective sections can be efficiently cleaned.

In the ultrasonic cleaning apparatus 10, the ultrasonic vibration units 21 are arranged at the proximity of the hand control part 42, the top end 44, and the connector 46, so that the cleaning can be concentrated at the respective sections; thus the entire endoscope 18 can be efficiently cleaned.

In the ultrasonic cleaning apparatus 10, since the cleaning vessel 16 is made of resin and is light-weighted, the ultrasonic cleaning apparatus 10 can be light-weighted in its entirety. Moreover, the cleaning vessel 16 is light-weighted, thus the position of the center of gravity of the entire ultrasonic cleaning apparatus 10 is lowered and the stability of the ultrasonic cleaning apparatus 10 is well. Since the cleaning vessel 16 is light-weighted, the frame for supporting the cleaning vessel 16 can be smaller, and thus the entire ultrasonic cleaning apparatus 10 can be small-sized.

The resin cleaning vessel 16 with a complex shape can be easily made; thus, the cleaning vessel 16 can be made to fit the complex shape of the endoscope 18.

The ultrasonic vibrators 24 of the ultrasonic wave cleaning apparatus 10 are attached to the cleaning vessel 16 through the diaphragms 22 and the elastic bodies 32; thus the ultrasonic vibrations that are applied to the cleaning vessel 16 from the ultrasonic vibrators 24 are attenuated by the diaphragms 22 and is attenuated further by the elastic bodies 32. By the above-described construction, uncertainty of the strength of the cleaning vessel 16 due to change of material from metal to the resin can be eliminated, and the thickness of the cleaning vessel 16 can be formed for example as thin as 3–5 mm.

The metal ultrasonic vibrators 24 are attached by adhering the vibrators 24 to the metal diaphragms 22; thus unlike the case where the metal ultrasonic vibrators 24 are adhered to the resin cleaning vessel 16, the ultrasonic vibrators 24 do not fall off the adhering face, which lowers cleaning efficiency.

In the ultrasonic cleaning apparatus 10, the vibrators 22 are disposed at the openings 16A of the cleaning vessel 16; thus unlike the case where the ultrasonic vibrators 24 are attached to the outer wall of the cleaning vessel 16, the ultrasonic waves are not absorbed by the resin cleaning vessel 16. Thereby the respective sections of the endoscope 18 can be cleaned by the ultrasonic waves radiated from the ultrasonic wave vibrators 24.

Figure 5:
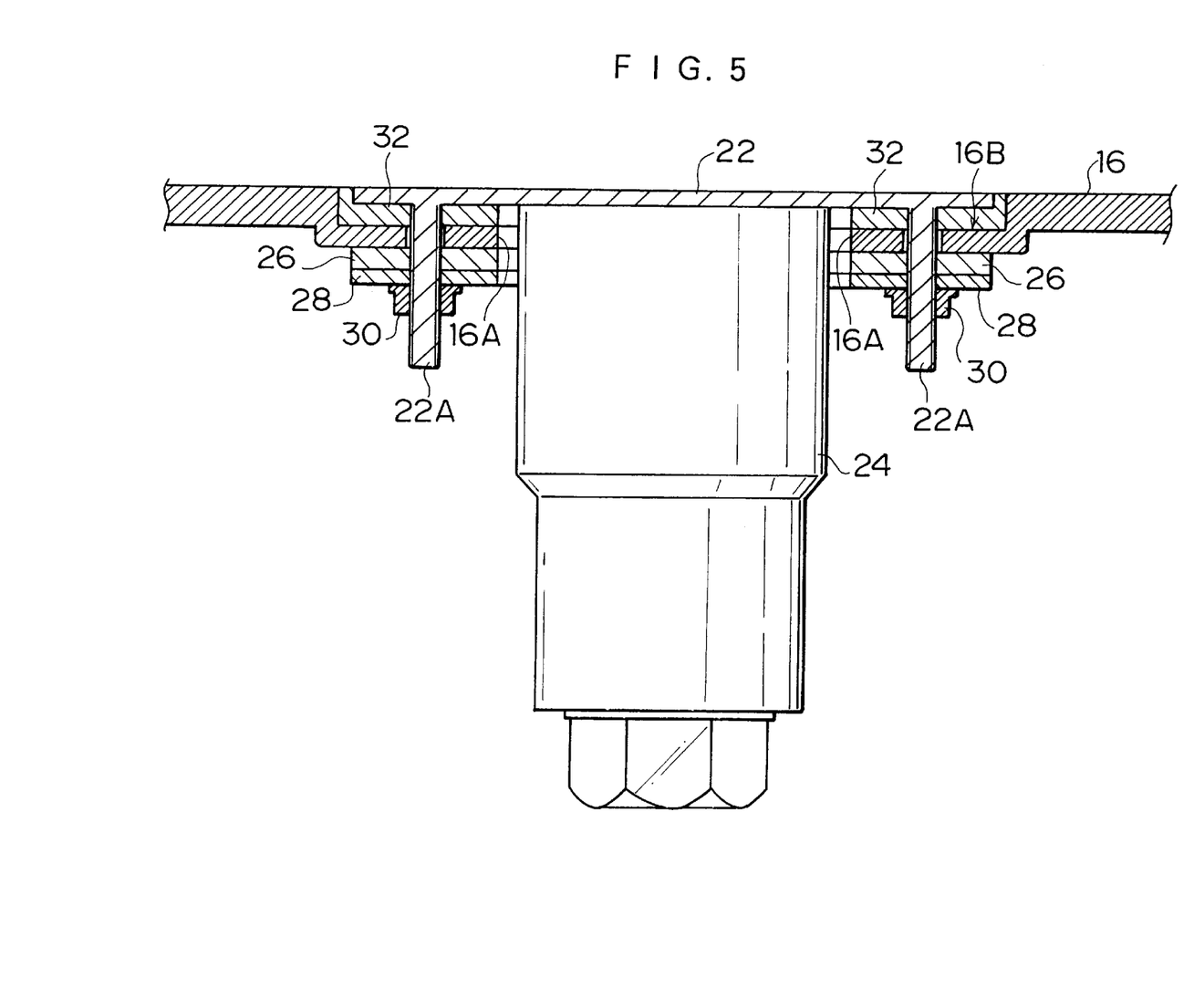
FIG. 5 is a longitudinal section view of an ultrasonic vibration units which is a unique part of the second embodiment of the ultrasonic cleaning apparatus for an endoscope of the present invention.

As shown in FIG. 5, the ultrasonic cleaning apparatus in the second embodiment has a sunken part 16B at the bottom of the cleaning vessel 16 in which the diaphragm 22 and the elastic body 32 are contained. By this structure the appearance of the bottom of the cleaning vessel 16 is flat without a step in order to prevent the contamination to be easily settled compared with the form of the bottom with a step, and also the contamination, if settled at the bottom of the cleaning vessel 16, can be easily washed out.

The present embodiment presents an example in which one endoscope 18 is cleaned; however, two endoscopes 18 and 18 may be cleaned at the same time. In such a case, the hand control part 42 of the second endoscope 18 is arranged at the upper part of the ultrasonic vibration unit 21 at the upper right side in FIG. 2, and the top end part 44 is arranged at the upper part of the ultrasonic vibration unit 21 at the upper left side in FIG. 2. The ultrasonic vibration unit 21 at the upper right side radiates an ultrasonic wave of a suitable frequency for cleaning the hand control part 42, while the ultrasonic vibration unit 21 at the upper left side radiates an ultrasonic wave of a suitable frequency for cleaning the top end part 44; whereby the two endoscopes 18 and 18 can be cleaned at the same time.

The present embodiment uses the ultrasonic vibration units 21 which are a part of the bottom of the cleaning vessel 16; however, another ultrasonic vibration unit of a type which is immersed into the antiseptic solution in the cleaning vessel 16 can also be used for achieving the same effect as the one described above.

Number and arrangement of the ultrasonic vibrators 24 are not limited to the manner described in the above embodiment. For example, the ultrasonic vibration units 21 are arranged at the bottom and the side faces of the cleaning vessel 16 by the same numbers, and the ultrasonic vibrators 24 may be controlled to be activated in accordance with the positions of the respective sections of the contained endoscope 18. Thereby, the endoscope 18 with insertion part of different lengths can be efficiently cleaned.

Furthermore, in the present embodiment, the respective ultrasonic vibrators 24 radiate ultrasonic waves of different frequencies corresponding with the respective section of the endoscope 18 one at a time in a certain time length. However, all ultrasonic vibrators 24 may radiate ultrasonic waves of a common frequency, or the individual ultrasonic vibrator 24 may always radiate an ultrasonic wave of the same frequency.

Figure 6:
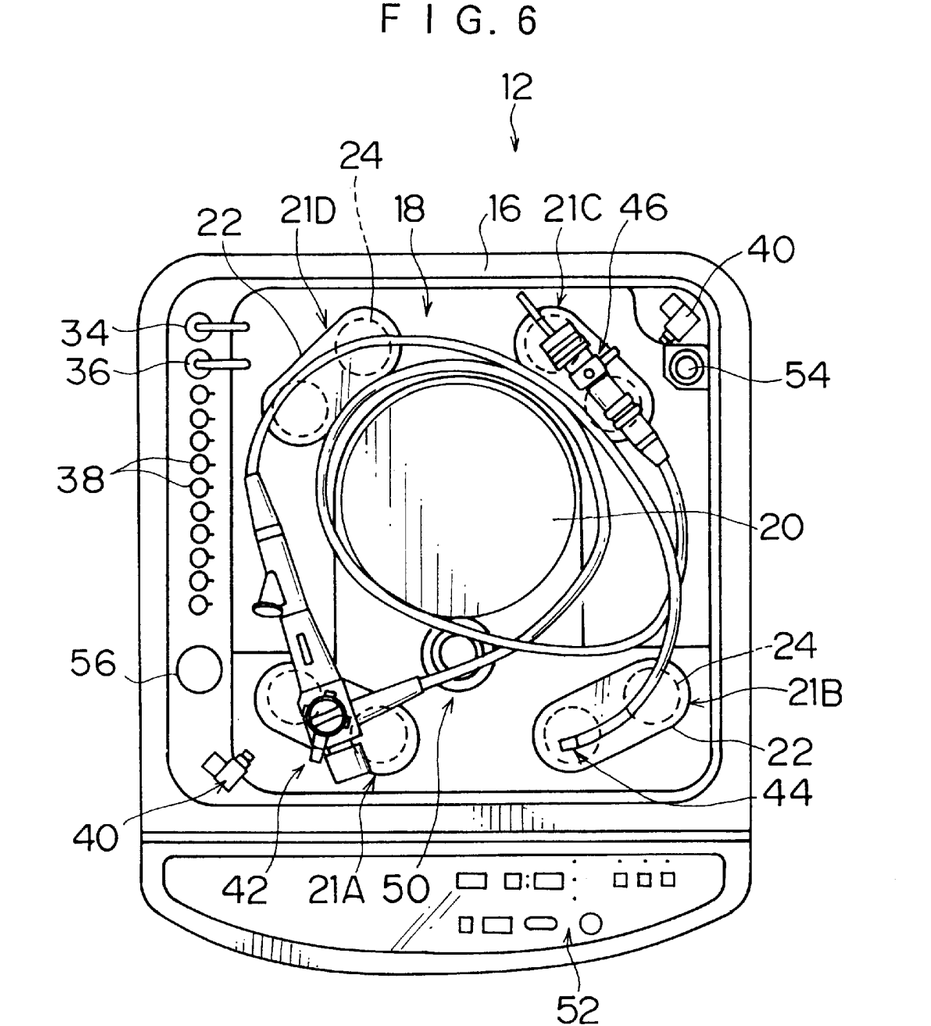
FIG. 6 is a plan view showing the third embodiment of the ultrasonic cleaning apparatus for an endoscope of the present invention.

FIG. 6 is a plan view showing the ultrasonic cleaning apparatus in the third embodiment. The members which are the same or similar as the ones in the first embodiment in FIG. 2 are assigned the same numbers and characters, and the description for them is omitted.

As shown in FIG. 6, four ultrasonic vibration units 21A, 21B, 21C, and 21D are disposed at the bottom of the cleaning vessel 16. The ultrasonic vibration units 21A–21C are disposed at the proximity of the sections where the contamination of the endoscope 18 contained in the cleaning vessel 16 is high. More specifically, the ultrasonic vibration unit 21A is arranged at the hand control part 52 of the endoscope 18, the ultrasonic vibration unit 21B is arranged at the top end part 44 of the insertion part, and the ultrasonic vibration unit 21C is arranged at the connector 46. The ultrasonic vibration unit 21D which is disposed at the corner of the upper left side of the cleaning vessel 16 is used in a case when the two endoscopes 18 are cleaned at the same time.

The ultrasonic vibration units 21A–21D respectively have diaphragms 23 and the two ultrasonic vibrators 24 and 24. Similar as the diaphragms 22 in FIG. 3, the diaphragms 23 are placed so as to block the circular opening 16A which is formed at the bottom of the cleaning vessel 16. The diaphragm 23 is made of metal such as stainless steel or titanium, and is fixed to the cleaning vessel 16 by tightening the nut 30 to the bolt 22A which projects to the bottom via the back packing 26 and the pressing plate 28. The elastic body 32 is disposed in between the diaphragm 23 and the cleaning vessel 16, whereby the gap between the diaphragm 23 and the cleaning vessel 16 is sealed by the elastic body 32.

In the ultrasonic cleaning apparatus in the third embodiment which is constructed as described above, the two ultrasonic vibrators 24 and 24 which radiate the ultrasonic waves of different frequencies are attached to one of the diaphragm 23; thus a computed intermingled wave can be formed, and the top end 44 can be efficiently cleaned by the intermingled wave.

The ultrasonic cleaning apparatus in the third embodiment uses the resin cleaning vessel 16 which does not easily transmit the ultrasonic waves. Thus, the ultrasonic vibrations from the respective ultrasonic vibration units 21A–21C are transmitted through the cleaning vessel 16, so that the ultrasonic waves can be inhibited from interfering each other. Moreover, the ultrasonic vibrators 24 are attached to the cleaning vessel 16 through the diaphragm 23 and the elastic body 32; thus the ultrasonic vibration transmitted from the ultrasonic vibrators 24 to the cleaning vessel 16 is attenuated by the diaphragm 23 and the elastic body 32, so that the effect to inhibit the ultrasonic waves improves. Further, the ultrasonic vibration units 21A–21C are arranged at the respective corners of the bottom of the cleaning vessel 16, and the ultrasonic vibration units 21A–21C are separated from each other, thus the interference of the ultrasonic waves can be better inhibited. The cleaning efficiency is not lowered by the interference of the ultrasonic waves even though the ultrasonic vibration units 21A–21C radiate ultrasonic waves of different frequencies. Thereby the ultrasonic waves of frequencies which are respectively suitable for the respective section of the endoscope 18 are radiated from the ultrasonic vibration units 21A–21C and the entire endoscope 18 can be cleaned in a short period of time.

In the ultrasonic cleaning apparatus in the third embodiment, the ultrasonic waves radiated from the ultrasonic vibration units 21A–21C do not interfere with each other. Thus in a case where the two ultrasonic wave vibrators 24 and 24 attached to one diaphragm 23 radiate ultrasonic waves of different frequencies, the computed intermingled wave can be formed without noise. Because the cleaning effects of the ultrasonic waves of two sorts of frequencies can be achieved, the endoscope 18 can be cleaned in a short period of time.

In a case where the ultrasonic vibration unit 21D is used in addition to the ultrasonic vibration units 21A–21C when the two endoscopes 18 are cleaned at the same time, the ultrasonic waves radiated from the ultrasonic vibration units 21A–21D also do not interfere with each other.

The materials of the cleaning vessel 16 in the third embodiment is not limited to resin, however, material which does not easily transmit ultrasonic vibrations is preferred.

The structures of the ultrasonic wave vibration units 21A–21D are not limited to the ones described above. For example, one, three, or more ultrasonic vibrator(s) may be attached.

As described above, the ultrasonic cleaning apparatus for an endoscope of the present invention uses a resin cleaning vessel so as to prevent interference of the ultrasonic waves while the ultrasonic vibrators are disposed at the position where the contamination is high in the endoscope; thereby the ultrasonic waves without interference is radiated the efficient cleaning can be achieved.

Further, according to the present invention, the cleaning vessel is made of synthetic resin in order to make the tub light-weighted, which achieves the ultrasonic cleaning apparatus to be light in weight in its entirety and to be small-sized. The ultrasonic vibrators of the present invention are attached to the cleaning vessel through the diaphragms, so that damage of the cleaning vessel and the separation of the ultrasonic vibrators can be prevented.

Furthermore, the ultrasonic waves of different frequencies corresponding with the respective sections of the endoscope are radiated, whereby the entire endoscope can be efficiently cleaned in a short period of time.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An ultrasonic cleaning apparatus for an endoscope, comprising:
   a cleaning vessel made of synthetic resin, the cleaning vessel holding a cleaning liquid in which the endoscope is immersed; and
   an ultrasonic generator which applies ultrasonic waves to the cleaning liquid so as to clean the endoscope, the ultrasonic generator comprising an ultrasonic vibrator and a diaphragm, the ultrasonic vibrator being attached to the cleaning vessel through the diaphragm,
   wherein an elastic body is arranged between the diaphragm and the cleaning vessel;
   wherein a nut tightens to a bolt of the diaphragm; and
   wherein a packing is arranged between the cleaning vessel and the nut.

2. The ultrasonic cleaning apparatus as defined in claim 1, wherein the ultrasonic generator is arranged to face a region of the endoscope contained in the cleaning vessel where contamination is high.

3. The ultrasonic cleaning apparatus as defined in claim 1, wherein the diaphragm is made of metal.

4. The ultrasonic cleaning apparatus as defined in claim 1, further comprising at least one additional ultrasonic generator applying ultrasonic waves of a different frequency from the former ultrasonic generator.

5. The ultrasonic cleaning apparatus as defined in claim 4, wherein the ultrasonic generators are arranged to face a top end, a hand control part, and a connector, respectively, of the endoscope.

6. The ultrasonic cleaning apparatus as defined in claim 1, wherein the ultrasonic generator further comprises an additional ultrasonic vibrator applying ultrasonic waves of a different frequency from the former ultrasonic vibrator, the additional ultrasonic vibrator being attached to the cleaning vessel through the diaphragm.

7. The ultrasonic cleaning apparatus as defined in claim 1, wherein a gap is provided between the cleaning vessel and the ultrasonic generator and an opening in the cleaning vessel.

8. The ultrasonic cleaning apparatus as defined in claim 1, wherein a pressing plate is provided between the packing and the nut.

9. The ultrasonic cleaning apparatus as defined in claim 1, wherein the synthetic resin is selected from the group consisting of fiber glass reinforced plastics, polyacetal, polyphenyleneoxide, acrylonitrile-butadiene-styrene copolymer, polyethylene, polypropylene, polytetrafluoroethylene and polycarbonate.

10. The ultrasonic cleaning apparatus as defined in claim 1, wherein the elastic body is selected from the group consisting of fluoric rubber, silicone rubber, ethylene-propylene-diene-methylene, ethylene-propylene-terpolymer, silicone filler, elastic fluoric resin and neoprene rubber.

* * * * *